United States Patent
Kato et al.

(10) Patent No.: US 10,087,274 B2
(45) Date of Patent: Oct. 2, 2018

(54) SILICONE HYDROGEL, MEDICAL DEVICE, LENS FOR EYE AND CONTACT LENS

(71) Applicant: TORAY INDUSTRIES, INC., Tokyo (JP)

(72) Inventors: Tomohiro Kato, Otsu (JP); Kazuhiko Fujisawa, Otsu (JP); Masataka Nakamura, Otsu (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 15/321,516

(22) PCT Filed: Jun. 16, 2015

(86) PCT No.: PCT/JP2015/067320
§ 371 (c)(1),
(2) Date: Dec. 22, 2016

(87) PCT Pub. No.: WO2015/198919
PCT Pub. Date: Dec. 30, 2015

(65) Prior Publication Data
US 2017/0204213 A1    Jul. 20, 2017

(30) Foreign Application Priority Data

Jun. 27, 2014 (JP) .................. 2014-132299
Dec. 17, 2014 (JP) .................. 2014-254863

(51) Int. Cl.
| | | |
|---|---|---|
| C08F 230/08 | (2006.01) | |
| G02B 1/04 | (2006.01) | |
| A61L 27/18 | (2006.01) | |
| A61L 27/52 | (2006.01) | |
| C08F 20/26 | (2006.01) | |

(52) U.S. Cl.
CPC ............ *C08F 230/08* (2013.01); *A61L 27/18* (2013.01); *A61L 27/52* (2013.01); *C08F 20/26* (2013.01); *G02B 1/043* (2013.01); *A61L 2430/16* (2013.01)

(58) Field of Classification Search
CPC ....................................... G02B 1/043
USPC ................................. 523/106, 107
See application file for complete search history.

(56) References Cited

U.S. PATENT DOCUMENTS

| | | | |
|---|---|---|---|
| 4,525,563 A | 6/1985 | Shibata | |
| 7,396,890 B2 | 7/2008 | Zanini | |
| 8,703,891 B2 | 4/2014 | Broad | |
| 2002/0107324 A1* | 8/2002 | Vanderlaan | C08F 230/08 525/100 |
| 2003/0022984 A1 | 1/2003 | Kawase | |
| 2003/0125498 A1* | 7/2003 | McCabe | A61L 27/18 528/25 |
| 2003/0162862 A1* | 8/2003 | McCabe | A61L 27/18 523/106 |
| 2004/0122249 A1 | 6/2004 | Fujisawa | |
| 2008/0076883 A1 | 3/2008 | Takeuchi | |
| 2015/0368386 A1* | 12/2015 | Nicholson | G02B 1/043 524/547 |

FOREIGN PATENT DOCUMENTS

| | | |
|---|---|---|
| JP | 59185310 | 10/1984 |
| JP | 06245991 | 9/1994 |
| JP | 2002047365 | 2/2002 |
| JP | 2002241698 | 8/2002 |
| JP | 2002371116 | 12/2002 |
| JP | 2004075755 | 3/2004 |
| JP | 2007526364 | 9/2007 |
| JP | 2009197071 | 9/2009 |
| JP | 2010510550 | 4/2010 |
| WO | 2006001510 | 1/2006 |

OTHER PUBLICATIONS

International Search Report and Written Opinion for International Application No. PCT/JP2015/067320, dated Aug. 11, 2015, 6 pages.

* cited by examiner

*Primary Examiner* — Marc S Zimmer
(74) *Attorney, Agent, or Firm* — RatnerPrestia

(57) ABSTRACT

In order to provide a silicone hydrogel which has high uniformity in polymerization rates of polymerization components used for copolymerization, excellent mechanical characteristics, excellent optical characteristics and good shape recoverability and in order to also provide various medical devices and ocular lenses having an excellent balance among elasticity, wettability and transparency, the present invention provides a silicone hydrogel which has a repeating unit derived from a monofunctional linear silicone (meth)acrylate and a repeating unit derived from a hydrophilic (meth)acrylate, and wherein the content of the repeating units derived from (meth)acrylates is more than 80% by mass.

11 Claims, 1 Drawing Sheet

[Fig 1]
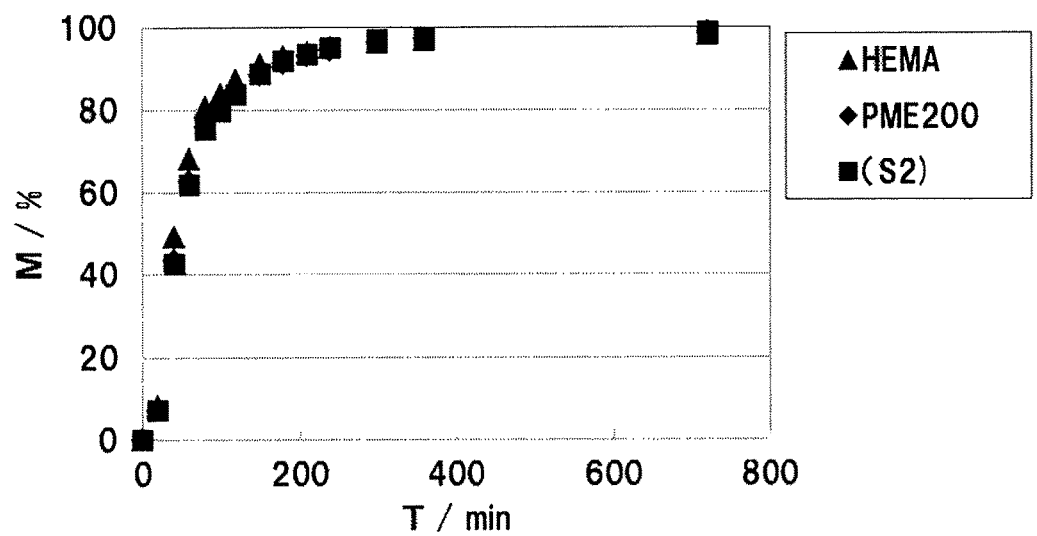
[Fig 2]
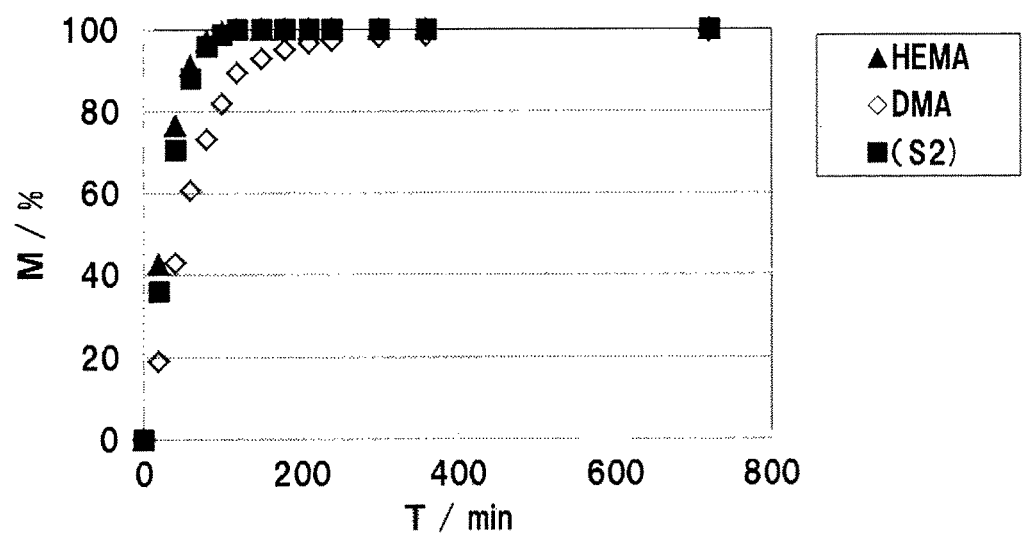

SILICONE HYDROGEL, MEDICAL DEVICE, LENS FOR EYE AND CONTACT LENS

CROSS REFERENCE TO RELATED APPLICATION

This is the U.S. National Phase application of PCT International Application No. PCT/JP2015/067320, filed Jun. 16, 2015, and claims priority to Japanese Patent Application No. 2014-132299, filed Jun. 27, 2014, and Japanese Patent Application No. 2014-254863, filed Dec. 17, 2014, the disclosures of each of these applications being incorporated herein by reference in their entireties for all purposes.

FIELD OF THE INVENTION

The present invention relates to a silicone hydrogel. The silicone hydrogel is suitable for use in medical devices such as lenses for eye, endoscopes, catheters, infusion tubes, gas transfer tubes, stents, sheaths, cuffs, tube connectors, access ports, drainage bags, blood circuits, vulnerary covering materials and various kinds of drug carriers, particularly in lenses for eye such as contact lenses, intraocular lenses and artificial corneas.

BACKGROUND OF THE INVENTION

In recent years, a silicone hydrogel has been known as a material of a contact lens to be used for continuous wearing. The silicone hydrogel is obtained by combining at least one silicone component and at least one hydrophilic component. For example, Patent Document 1 discloses a silicone hydrogel obtained by polymerizing a polymerization stock solution containing a silicone (meth)acrylamide, a silicone (meth)acrylate, and hydrophilic components which may include a hydrophilic acrylamide such as N,N-dimethylacrylamide, a hydrophilic methacrylate such as 2-hydroxyethyl methacrylate, and an internal humectant.

Patent Document 2 discloses a silicone hydrogel obtained by polymerizing a polymerization stock solution containing two silicone methacrylates, N-vinylpyrrolidone, and hydrophilic monomers such as 2-hydroxyethyl methacrylate and N,N-dimethylacrylamide.

However, these compositions have the problem that since a silicone monomer, a hydrophilic monomer and a crosslinking monomer have mutually different polymerizable groups such as an acrylamide and a methacrylate, the polymerization rates of the monomers during copolymerization are not equal, and thus the resulting silicone hydrogel has different compositions in the initial stage of polymerization and the late stage of polymerization. Silicone hydrogels obtained from compositions as described above may have a problem in mechanical properties and optical properties.

Example 13 in Patent Document 3 discloses a composition with two silicone methacrylates of monofunctional branched type: 3-tris(trimethylsiloxy)silylpropyl methacrylate and 3-[3-methylbis(trimethylsiloxy)silylpropoxy]propyl (meth)acrylate; 2-hydroxyethyl methacrylate as a hydrophilic methacrylate; and ethylene glycol dimethacrylate as a dimethacrylate-based crosslinking monomer. Each of the polymerizable groups of various monomers to be used in this composition is a methacrylate, so that the resulting silicone hydrogel has a uniform composition in the initial stage of polymerization and the late stage of polymerization, leading to improvement of mechanical properties and optical properties.

PATENT DOCUMENTS

Patent Literature 1: Kohyo (National Publication of Translated Version) No. 2007-526364
Patent Literature 2: Kohyo (National Publication of Translated Version) No. 2010-510550
Patent Literature 3: Japanese Patent Laid-open Publication No. 2002-47365

SUMMARY OF THE INVENTION

However, the present inventors have found that the composition in Example 13 in Patent Document 3 has a problem in shape recovery properties. This may be because although each of the polymerizable groups of monomers to be used for obtaining the composition is a methacrylate, interaction such as hydrogen bonding of ester groups contained in the methacrylate is relatively small, and thus interaction between polymer chains is not sufficient.

An object of the present invention is to provide a silicone hydrogel which has high uniformity of polymerization rates of polymerization components to be used for copolymerization, excellent mechanical properties and optical properties, and favorable shape recovery properties. Also, an object of the present invention is to provide various medical devices and lenses for eye such as contact lenses, intraocular lenses and artificial corneas, which are excellent in balance among an elastic modulus, wettability and transparency.

In order to achieve the above objects, the present inventors have extensively conducted studies. The present inventors have given attention to the molecular structure of monofunctional silicone, and found that when the silicone is linear rather than being branched, shape recovery properties are efficiently improved. The present invention includes the following constitutions.

(1) A silicone hydrogel including a repeating unit derived from a monofunctional linear silicone (meth)acrylate and a repeating unit derived from a hydrophilic (meth)acrylate, wherein
the content of the repeating units derived from the (meth)acrylates is more than 80% by mass.
(2) The silicone hydrogel according to (1), wherein the monofunctional linear silicone (meth)acrylate is represented by the following general formula (a):

[Chemical Formula 1]

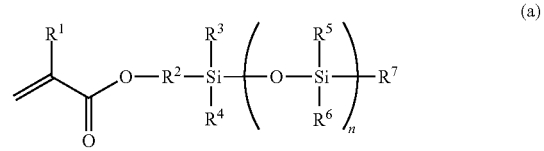

(a)

wherein $R^1$ represents hydrogen or a methyl group; $R^2$ represents an optionally substituted divalent organic group having 1 to 20 carbon atoms; $R^3$ to $R^6$ each independently represent an optionally substituted alkyl group having 1 to 20 carbon atoms or an optionally substituted aryl group having 6 to 20 carbon atoms; $R^7$ represents an optionally substituted alkyl group having 1 to 20 carbon atoms or an optionally substituted aryl group having 6 to 20 carbon atoms; and n represents an integer of 1 to 200 which optionally has distribution.

(3) The silicone hydrogel according to (1) or (2), further including a repeating unit derived from a monofunctional silicone (meth)acrylate different from the monofunctional linear silicone (meth)acrylate.
(4) The silicone hydrogel according to any one of (1) to (3), wherein the content of the repeating unit derived from the silicone (meth)acrylate is 30 to 95% by mass.
(5) The silicone hydrogel according to any one of (1) to (4), wherein the hydrophilic (meth)acrylate has a group selected from the group consisting of a hydroxyl group, an alkoxy group, a carboxy group and a sulfonic acid group in the molecule.
(6) The silicone hydrogel according to any one of (1) to (5), wherein the content of the repeating unit derived from the hydrophilic (meth)acrylate is 5 to 70% by mass.
(7) The silicone hydrogel according to any one of (1) to (6), including a repeating unit derived from a hydrophilic (meth)acrylate having no hydroxyl group, wherein the ratio of the repeating unit derived from the hydrophilic (meth)acrylate having no hydroxyl group in the repeating units derived from the hydrophilic (meth)acrylates is 20% by mass or more.
(8) The silicone hydrogel according to any one of (1) to (7), including a repeating unit derived from a polyfunctional (meth)acrylate.
(9) The silicone hydrogel according to (9), wherein the content of the repeating unit derived from the polyfunctional (meth)acrylate is 0.05 to 10% by mass.

A silicone hydrogel of the present invention has high uniformity of polymerization rates of polymerization components to be used for copolymerization, excellent mechanical properties and optical properties, and favorable shape recovery properties. The silicone hydrogel of the present invention is excellent in balance among an elastic modulus, wettability and transparency, and can be suitably used in various medical devices and lenses for eye such as contact lenses, intraocular lenses and artificial corneas.

BRIEF DESCRIPTION OF THE DRAWINGS

FIG. 1 shows a monomer consumption rate curve in Example 18.
FIG. 2 shows a monomer consumption rate curve in Comparative Example 2.

DETAILED DESCRIPTION OF EMBODIMENTS OF THE INVENTION

The term "(meth)" or "(methyl)" used in this specification refers to optional methylation. Thus, for example, the term "(meth)acrylate" refers to both a methacrylate and an acrylate. The same applies to the terms "(meth)acrylic acid", "(meth)acrylamide", "(meth)acryloyl" and so on.

The term "(meth)acrylate" used in this specification refers to an (meth)acrylic acid ester.

The term "monomer" used in this specification refers to a compound having one or more radically polymerizable functional groups.

The term "repeating unit" used in this specification refers to one unit of a repeating structure derived from a monomer structure.

The silicone hydrogel according to aspects of the present invention is a silicone hydrogel which includes a repeating unit derived from a monofunctional linear silicone (meth)acrylate used as a monomer component and a repeating unit derived from a hydrophilic (meth)acrylate used as a monomer component and in which the content of the repeating units derived from the (meth)acrylates is more than 80% by mass based on the amount of the silicone hydrogel, namely a silicone hydrogel obtained by polymerizing a polymerization stock solution in which the content of (meth)acrylate-based monomer components is more than 80% by mass based on the amount of all monomer components. In this specification, the "mass of silicone hydrogel" is a mass of only a polymer backbone which excludes the mass of volatile components such as water. In this specification, the term "(meth)acrylate" refers to a collection of monomers having a (meth)acrylate group, and the term "content of repeating units derived from a (meth)acrylate" refers to the total content of repeating units derived from monomers having a (meth)acrylate group. The same applies to the "silicone (meth)acrylate", "hydrophilic (meth)acrylate" and so on, and the content of repeating units when two or more of these monomers are used is the total content of repeating units derived from monomers that satisfy the definition described above.

Here, for the "repeating unit derived from . . . " in the present invention, the "repeating unit derived from a monofunctional linear silicone (meth)acrylate", the "repeating unit derived from a hydrophilic (meth)acrylate", the "repeating unit derived from a (meth)acrylate" are each referred to as a "repeating unit derived from a monomer" for the sake of convenience. In the present invention, the "repeating unit derived from a monomer" is a structural unit in a polymer, which is generated with a radically polymerizable functional group changed through a polymerization reaction in polymerization of a radically polymerizable monomer and which corresponds to the structure of the monomer.

The "repeating unit derived from a monomer" is a structural unit represented by the following formula (y), the structural unit being generated with a radically polymerizable functional group changed through a polymerization reaction in polymerization of a radically polymerizable monomer represented by the following formula (x).

[Chemical Formula 2]

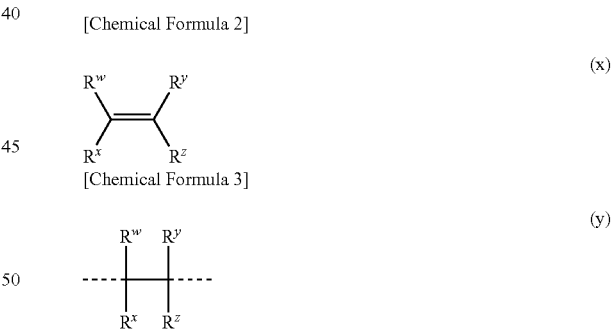

[Chemical Formula 3]

In the above formulae (x) and (y), Rw, Rx, Ry and Rz may each independently represent a group which ensures that a monomer represented by the above formula (x) is a radically polymerizable monomer.

The "repeating unit derived from a monomer" is not necessarily required to be formed by a method in which a monomer is copolymerized directly with other monomer to obtain a silicone hydrogel, and the "repeating unit derived from a monomer" may be formed by, for example, a method in which a macromonomer is prepared by introducing a (meth)acryloyloxy group into an intermediate polymer obtained by radically polymerizing a monomer, and the macromonomer is copolymerized with other monomer to obtain a silicone hydrogel.

In the case of, for example, a monofunctional linear silicone (meth)acrylate, when a method in which a monomer is copolymerized directly with other monomer to obtain a hydrogel is used, the repeating unit derived from a monofunctional linear silicone (meth)acrylate is a structural unit obtained by polymerizing a monofunctional linear silicone (meth)acrylate with other monomer into a silicone hydrogel, i.e. a structural unit in a polymer with a radically polymerizable functional group changed through a polymerization reaction in polymerization of a polymerization stock solution containing a monofunctional linear silicone methacrylate as shown in Example 1. When a method in which a macromonomer is prepared from a monomer, and the macromonomer is copolymerized with other monomer to obtain a silicone hydrogel is used, the repeating unit derived from a monofunctional linear silicone (meth)acrylate is first formed in an intermediate polymer obtained by radically polymerizing the monofunctional linear silicone (meth)acrylate. A macromonomer prepared by introducing a (meth)acryloyloxy group into the intermediate polymer is polymerized with other monomer into a silicone hydrogel, whereby a silicone hydrogel including a structural unit derived from a monofunctional linear silicone (meth)acrylate can be obtained.

In the present invention, the silicone monomer refers to a monomer containing a polymerizable group and a siloxanyl group. The siloxanyl group refers to a group having at least one Si—O—Si bond.

In the present invention, the term "monofunctional" means that only one radically polymerizable functional group [e.g. (meth)acryloyloxy group] exists in the molecule.

In the present invention, the silicone (meth)acrylate refers to a monomer containing a (meth)acryloyloxy group and a siloxanyl group.

The linear silicone in a monofunctional linear silicone (meth)acrylate refers to a structure in which when a line is drawn along a siloxanyl bond (bond formed by repetition of —Si—O—) in silicone with a silicon atom as a starting point, the silicon atom being bonded to an organic group having a (meth)acryloyloxy group, the line is formed as a single line having no branch. In other words, the monofunctional linear silicone (meth)acrylate or the linear silicone (meth)acrylate refers to a structure represented by the following general formula (p).

[Chemical Formula 4]

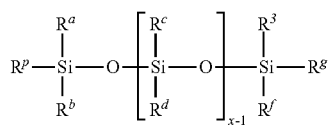

(p)

In the formula (p), $R^p$ represents an alkyl group having a (meth)acryloyloxy group. $R^a$ to $R^g$ each represent a group having no silicon atom, and x represents an integer of 2 or more.

The silicone hydrogel of the present invention includes a repeating unit derived from a monofunctional linear silicone (meth)acrylate.

In the present invention, the branched silicone in a monofunctional branched silicone (meth)acrylate refers to a structure in which when a line is drawn along a siloxanyl bond with a silicon atom as a starting point, the silicon atom being bonded to an organic group having a (meth)acryloyloxy group, the line extends in two or more directions, and/or the line has at least one branch, and thus cannot be expressed as a single line.

The monofunctional linear silicone (meth)acrylate to be used in the silicone hydrogel of the present invention is, for example, a monomer represented by the following general formula (a).

[Chemical Formula 5]

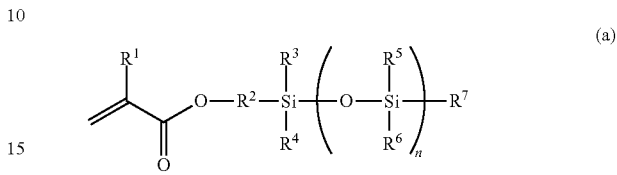

(a)

wherein $R^1$ represents hydrogen or a methyl group; $R^2$ represents an optionally substituted divalent organic group having 1 to 20 carbon atoms; $R^3$ to $R^6$ each independently represent an optionally substituted alkyl group having 1 to 20 carbon atoms, or an optionally substituted aryl group having 6 to 20 carbon atoms; $R^7$ represents an optionally substituted alkyl group having 1 to 20 carbon atoms, or an optionally substituted aryl group having 6 to 20 carbon atoms; and n represents an integer of 1 to 200 which optionally has distribution.

In the formula (a), $R^1$ represents hydrogen or a methyl group. Among them, a methyl group is more preferable because stickiness of the surface of the resulting silicone hydrogel is easily suppressed.

$R^2$ represents an optionally substituted divalent organic group having 1 to 20 carbon atoms; Examples thereof include alkylene groups such as a methylene group, an ethylene group, a propylene group, a butylene group, a pentylene group, an octylene group, a decylene group, a dodecylene group and an octadecylene group; and arylene groups such as a phenylene group and a naphthylene group. These alkylene groups and arylene groups may be linear or branched. When the number of carbon atoms in the divalent organic group is excessively large, compatibility with a hydrophilic monomer is hardly obtained, and when the number of carbon atoms in the divalent organic group is excessively small, the elongation of the resulting silicone hydrogel is reduced, so that the silicone hydrogel is easily broken. Therefore, the number of carbon atoms is more preferably 1 to 12, most preferably 2 to 8.

When the divalent organic group is substituted, examples of the preferred substituent include substituents such as a hydroxyl group, a carboxyl group, a sulfonic acid group, a phosphoric acid group, an ester, an ether, an amide and a combination thereof. Among them, a hydroxyl group, an ester, an ether and an amide are preferable from the viewpoint of improving a silicone moiety is hardly decomposed, and a hydroxyl group and an ether are further preferable because the transparency of the resulting silicone hydrogel is improved.

More preferred examples of $R^2$ include an ethylene group, a propylene group, a butylene group, and divalent organic groups represented by the following formulae (a1) to (a4):

   (a1)

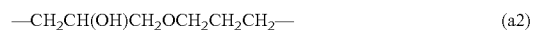   (a2)

   (a3)

   (a4).

Particularly, a propylene group, and divalent organic groups represented by the formulae (a1) to (a4) are preferable, and a propylene group and a divalent organic group represented by the formula (a2) are most preferable.

$R^3$ to $R^6$ each independently represent an optionally substituted alkyl group having 1 to 20 carbon atoms, or an optionally substituted aryl group having 6 to 20 carbon atoms. Examples thereof include a methyl group, an ethyl group, a n-propyl group, an isopropyl group, a n-butyl group, a s-butyl group, a t-butyl group, a n-pentyl group, an isopentyl group, a s-pentyl group, a neopentyl group, a hexyl group, a heptyl group, an octyl group, a nonyl group, a decyl group, a dodecyl group, an eicosyl group, a phenyl group and a naphthyl group. These alkyl groups and aryl groups may be linear or branched. When the number of carbon atoms is excessively large, the silicone content becomes relatively low, so that the oxygen permeability of the resulting silicone hydrogel is reduced, and therefore the number of carbon atoms is more preferably 1 to 12, still more preferably 1 to 6, and most preferably 1 to 4.

$R^7$ represents an optionally substituted alkyl group having 1 to 20 carbon atoms, or an optionally substituted aryl group having 6 to 20 carbon atoms. When the number of carbon atoms in $R^7$ is excessively small, the polysiloxane chain is easily hydrolyzed, and when the number of carbon atoms in the $R^7$ is excessively large, the oxygen permeability of the silicone hydrogel tends to be reduced. Accordingly, $R^7$ is more preferably an alkyl group having 1 to 10 carbon atoms or an aryl group having 6 to 10 carbon atoms, still more preferably an alkyl group having 1 to 6 carbon atoms, and most preferably an alkyl group having 1 to 4 carbon atoms. Preferred examples of the alkyl group having 1 to 20 carbon atoms or aryl group having 6 to 20 carbon atoms include a methyl group, an ethyl group, a n-propyl group, an isopropyl group, a n-butyl group, a s-butyl group, a t-butyl group, a n-pentyl group, an isopentyl group, a s-pentyl group, a neopentyl group, a hexyl group, a heptyl group, an octyl group, a nonyl group, a decyl group, a dodecyl group, an eicosyl group, a phenyl group and a naphthyl group. These alkyl groups and aryl groups may be linear or branched.

In the formulae (a1) to (a4), n represents an integer of 1 to 200 which optionally has distribution. When n is excessively large, a silicone moiety that is hydrophobic becomes excessively large, leading to deterioration of compatibility with a hydrophilic monomer, and when n is excessively small, sufficient oxygen permeability and shape recovery properties are not obtained. Therefore, n is more preferably 1 to 100, still more preferably 2 to 50, and most preferably 3 to 20. The lower limit is preferably 1, 2 or 3. The upper limit is preferably 100, 50 or 20. The above lower limit and the above upper limit may be combined in various ways. It is to be noted that when integer n has distribution, n is determined on the basis of the number average molecular weight of a monofunctional linear silicone (meth)acrylate.

The monofunctional linear silicone (meth)acrylate to be used in the silicone hydrogel of the present invention may be used alone, or in combination of n different kinds thereof.

The monofunctional linear silicone (meth)acrylate to be used in the silicone hydrogel of the present invention may be used in combination of a plurality of kinds of monofunctional linear silicone (meth)acrylates having mutually different chemical structures (the number of the kinds is not limited to n).

The silicone hydrogel of the present invention may further include, in addition to a repeating unit derived from a monofunctional linear silicone (meth)acrylate, a repeating unit derived from a monofunctional silicone (meth)acrylate different from the monofunctional linear silicone (meth)acrylate.

Examples of the different monofunctional silicone (meth)acrylate here include monofunctional branched silicone (meth)acrylates. Among the monofunctional branched silicone (meth)acrylates, monofunctional branched silicone (meth)acrylates represented by the following general formula (b) are preferable.

[Chemical Formula 6]

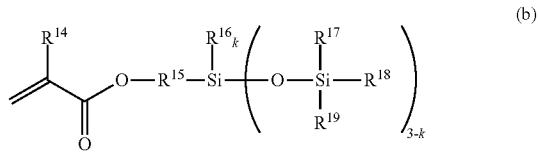

(b)

wherein $R^{14}$ represents hydrogen or a methyl group; $R^{15}$ represents an optionally substituted divalent organic group having 1 to 20 carbon atoms; $R^{16}$ to $R^{19}$ each independently represent an alkyl group having 1 to 20 carbon atoms, or an aryl group having 6 to 20 carbon atoms; and k represents an integer of 0 to 2.

In the formula (b), $R^{14}$ represents hydrogen or a methyl group. The monofunctional branched silicone (meth)acrylate is preferably a group having the same polymerization property as that of the monofunctional linear silicone (meth)acrylate for improving uniformity of polymerization of the resulting silicone hydrogel.

In the formula (b), $R^{15}$ represents an optionally substituted divalent organic group having 1 to 20 carbon atoms. Examples thereof include alkylene groups such as a methylene group, an ethylene group, a propylene group, a butylene group, a pentylene group, an octylene group, a decylene group, a dodecylene group and an octadecylene group; and arylene groups such as a phenylene group and a naphthylene group. These alkylene groups and arylene groups may be linear or branched. When the divalent organic group has an excessively large number of carbon atoms, compatibility with a hydrophilic monomer is hardly obtained, and when the number of carbon atoms in the divalent organic group is excessively small, the elongation of the resulting silicone hydrogel is reduced, so that the silicone hydrogel is easily broken. Therefore, the number of carbon atoms is more preferably 1 to 12, most preferably 2 to 8.

When the divalent organic group is substituted, examples of the preferred substituent include substituents such as a hydroxyl group, a carboxyl group, a sulfonic acid group, a phosphoric acid group, an ester, an ether, an amide and a combination thereof. Among them, a hydroxyl group, an ester, an ether and an amide are preferable because a silicone moiety is hardly decomposed, and a hydroxyl group and an ether are further preferable because the transparency of the resulting silicone hydrogel is improved.

More preferred examples of $R^{15}$ include an ethylene group, a propylene group, a butylene group, and divalent organic groups represented by the following formulae (b1) to (b4):

    (b1)

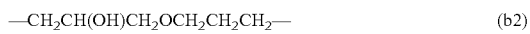    (b2)

    (b3)

    (b4).

Particularly, a propylene group, and divalent organic groups represented by the formulae (b1) to (b4) are preferable, and a propylene group and a divalent organic group represented by the formula (b2) are most preferable.

In the formula (b), $R^{16}$ to $R^{19}$ each independently represent an alkyl group having 1 to 20 carbon atoms, or an aryl group having 6 to 20 carbon atoms. When the number of carbon atoms in $R^{16}$ to $R^{19}$ is excessively large, the oxygen permeability of the silicone hydrogel is reduced, and therefore each of $R^{16}$ to $R^{19}$ is more preferably an alkyl group having 1 to 10 carbon atoms or an aryl group shaving 6 to 10 carbon atoms, still more preferably an alkyl group having 1 to 4 carbon atoms, and most preferably a methyl group or an ethyl group.

In the formula (b), k represents an integer of 0 to 2. For the silicone hydrogel to have sufficient oxygen permeability, k is more preferably 0 or 1.

Preferred examples of the monofunctional branched silicone (meth)acrylate include 3-[3-methylbis(trimethylsiloxy)silylpropoxy]propyl methacrylate, 3-[3-tris(trimethylsiloxy)silylpropoxy]propyl (meth)acrylate, 3-methylbis(trimethylsiloxy)silylpropoxy (meth)acrylate and 3-tris(trimethylsiloxy)silylpropyl (meth)acrylate.

When the content of repeating units derived from silicone-based (meth)acrylates, i.e. the total amount of a repeating unit derived from a monofunctional linear silicone (meth)acrylate and a repeating unit derived from a "monofunctional silicone (meth)acrylate different from the monofunctional linear silicone (meth)acrylate", which are contained in the silicone hydrogel of the present invention, is excessively large, compatibility with a hydrophilic monomer is deteriorated, so that it is difficult to obtain a transparent silicone hydrogel. When the content of the repeating units is excessively small, the silicone content decreases, so that it is difficult to obtain a silicone hydrogel having sufficient oxygen permeability. Therefore, the content of the repeating units is preferably 30 to 95% by mass, more preferably 40 to 80% by mass, most preferably 50 to 70% by mass. The lower limit is preferably 30% by mass, more preferably 40% by mass, still more preferably 50% by mass. The upper limit is preferably 95% by mass, more preferably 80% by mass, still more preferably 70% by mass. The preferred lower limit and the preferred upper limit may be combined in various ways.

In the present invention, the mass of silicone hydrogel is a mass measured after a silicone hydrogel in a "wet state" as defined in examples is purged with a sufficient amount of pure water for a sufficient time so that constituent components of a borate buffer do not remain, and the silicone hydrogel is then brought into a "dry state" as defined in examples.

When the ratio of the repeating unit derived from a monofunctional linear silicone (meth)acrylate in the repeating unit derived from a monofunctional linear silicone (meth)acrylate and the repeating unit derived from a "monofunctional silicone (meth)acrylate different from the monofunctional linear silicone (meth)acrylate" is excessively small, a silicone hydrogel having sufficient shape recovery properties is not obtained. When the above-mentioned ratio is excessively large, compatibility with a hydrophilic monomer is deteriorated, so that it is difficult to obtain a transparent silicone hydrogel. The above-mentioned ratio is preferably 10 to 100% by mass, more preferably 20 to 80% by mass, most preferably 30 to 60% by mass.

The silicone hydrogel of the present invention includes a repeating unit derived from a hydrophilic (meth)acrylate. In the present invention, the hydrophilic (meth)acrylate is a hydrophilic monomer, and the hydrophilic monomer is a monomer that is uniformly dissolved when mixed with water at a monomer/water ratio of 10/90 (mass ratio) at 25° C. In the present invention, the silicone monomer (silicone (meth)acrylate) is a monomer component different from the hydrophilic (meth)acrylate, and even if a silicone monomer satisfies the definition of the hydrophilic monomer, the monomer is considered as a monomer component different from the hydrophilic (meth)acrylate when the monomer is a monomer having a siloxanyl group.

Preferred examples of the hydrophilic (meth)acrylate to be used in the silicone hydrogel of the present invention include hydrophilic (meth)acrylates having a group selected from the group consisting of a hydroxyl group, an alkoxy group, a carboxy group and a sulfonic acid group in the molecule.

Examples of the hydrophilic (meth)acrylate having a hydroxyl group in the molecule, among hydrophilic (meth)acrylates to be used in the silicone hydrogel of the present invention, include hydroxyalkyl (meth)acrylates such as 2-hydroxyethyl (meth)acrylate, 2-hydroxypropyl (meth)acrylate, 3-hydroxypropyl (meth)acrylate, 2,3-dihydroxypropyl (meth)acrylate and glycerol (meth)acrylate; and hydrophilic (meth)acrylates represented by the later-described general formula (c) and having hydrogen as $R^{13}$.

Examples of the hydrophilic (meth)acrylate having an alkoxy group in the molecule include (meth)acrylates having a structure in which the hydroxyl group of a hydroxyalkyl (meth)acrylate such as 2-hydroxyethyl (meth)acrylate, 2-hydroxypropyl (meth)acrylate, 3-hydroxypropyl (meth)acrylate, 2,3-dihydroxypropyl (meth)acrylate or glycerol (meth)acrylate is replaced by an alkoxy group; and hydrophilic (meth)acrylates represented by the later-described general formula (c) and having as $R^{13}$ a group other than hydrogen. In the present invention, the "(meth)acrylate having a structure in which the hydroxyl group is replaced by an alkoxy group" refers to a (meth)acrylate having the same structure as that of a (meth)acrylate obtained by replacing a hydroxyl group by an alkoxy group, and may be one obtained through another synthetic route which does not involve a hydroxyl group. The same applies to a "(meth)acrylate having a structure in which the hydroxyl group is replaced by a methoxy group" as described later.

Examples of the hydrophilic (meth)acrylate having a carboxy group in the molecule include carboxyalkyl (meth)acrylates such as 2-carboxyethyl (meth)acrylate and 3-carboxypropyl (meth)acrylate.

Examples of the hydrophilic (meth)acrylate having a sulfonic acid group in the molecule include sulfoalkyl (meth)acrylates such as 2-sulfoethyl (meth)acrylate and 3-sulfopropyl (meth)acrylate.

The hydrophilic (meth)acrylate to be used in the silicone hydrogel of the present invention may be used alone, or in combination of two or more hydrophilic (meth)acrylates.

The hydrophilic (meth)acrylate represented by the following general formula (c) is as follows.

[Chemical Formula 7]

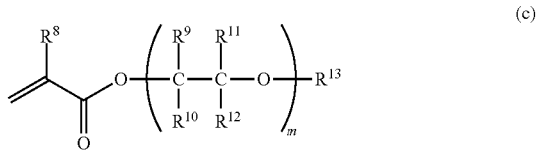

wherein $R^8$ represents hydrogen or a methyl group; $R^9$ to $R^{12}$ each independently represent hydrogen, an optionally substituted alkyl group having 1 to 20 carbon atoms, or an optionally substituted aryl group having 6 to 20 carbon atoms; $R^{13}$ represents hydrogen, an optionally substituted alkyl group having 1 to 20 carbon atoms, or an optionally substituted aryl group having 6 to 20 carbon atoms; and m represents an integer of 2 to 100 which optionally has distribution.

In the formula (c), $R^8$ represents a hydrogen atom or a methyl group. The monofunctional branched silicone (meth) acrylate is preferably a group having the same polymerization property as that of the monofunctional linear silicone (meth)acrylate for improving uniformity of polymerization of the resulting silicone hydrogel.

$R^9$ to $R^{12}$ each independently represent a hydrogen atom, an optionally substituted alkyl group having 1 to 20 carbon atoms, or an optionally substituted aryl group having 6 to 20 carbon atoms. Preferred examples of the alkyl group having 1 to 20 carbon atoms or aryl group having 6 to 20 carbon atoms include a methyl group, an ethyl group, a n-propyl group, an isopropyl group, a n-butyl group, a s-butyl group, a t-butyl group, a n-pentyl group, an isopentyl group, a s-pentyl group, a neopentyl group, a hexyl group, a heptyl group, an octyl group, a nonyl group, a decyl group, a phenyl group and a naphthyl group. These alkyl groups and aryl groups may be linear or branched. When the total number of carbon atoms in $R^9$ to $R^{12}$ in one repeating unit is excessively large, the hydrophilic property of the monomer represented by the formula (c) is deteriorated, and therefore the total number of carbon atoms in $R^9$ to $R^{12}$ is preferably 0 to 10, more preferably 0 to 5, still more preferably 0 to 1, and most preferably 0.

$R^{13}$ represents a hydrogen atom, an alkyl group having 1 to 20 carbon atoms, or an aryl group having 6 to 20 carbon atoms. Preferred examples of the alkyl group having 1 to 20 carbon atoms or aryl group having 6 to 20 carbon atoms include a methyl group, an ethyl group, a n-propyl group, an isopropyl group, a n-butyl group, a s-butyl group, a t-butyl group, a n-pentyl group, an isopentyl group, a s-pentyl group, a neopentyl group, a hexyl group, a heptyl group, an octyl group, a nonyl group, a decyl group, a dodecyl group, an eicosyl group, a phenyl group and a naphthyl group. These alkyl groups and aryl groups may be linear or branched. When the number of carbon atoms in $R^{13}$ is excessively large, the hydrophilic property of the monomer represented by the formula (c) is deteriorated, and therefore the number of carbons in $R^{13}$ is preferably 0 to 10, more preferably 0 to 5, still more preferably 0 to 2, and most preferably 0 to 1.

In the Formula 7, m represents an integer of 2 to 100. When the value of m is excessively large, compatibility with a silicone component is deteriorated, and when the value of m is excessively small, it is difficult to function as a hydrophilic monomer. Therefore, the value of m is more preferably 2 to 50, still more preferably 2 to 10, and most preferably 3 to 5. From the viewpoint of transparency, m is preferably 2 to 8, more preferably 2 to 6. The lower limit is 2 or 3. The upper limit is 100, 50, 10, 8, 6 or 5. The lower limit and the upper limit may be combined in various ways. When the value m has distribution, the value m is determined on the basis of the number average molecular weight of the hydrophilic monomer.

Examples of the hydrophilic (meth)acrylate represented by the general formula (c) include diethylene glycol mono(meth)acrylate, triethylene glycol mono(meth)acrylate, tetraethylene glycol (meth)acrylate, polyethylene glycol mono(meth)acrylate and the like which are collectively called a polyethylene glycol mono(meth)acrylate, and (meth)acrylates having a structure in which the hydroxyl group of a polyethylene glycol mono(meth)acrylate is replaced by an alkoxy group; and dipropylene glycol mono(meth)acrylate, tripropylene glycol mono(meth)acrylate, tetrapropylene glycol mono(meth)acrylate, polypropylene glycol mono(meth)acrylate and the like which are collectively called polypropylene glycol mono(meth)acrylate, and (meth)acrylates having a structure in which the hydroxyl group of a polypropylene glycol mono(meth)acrylate is replaced by an alkoxy group.

Among hydrophilic (meth)acrylates, (meth)acrylates having a hydroxyl group in the molecule and (meth)acrylates having an alkoxy group in the molecule are preferable for ensuring that the silicone component of the resulting silicone hydrogel is hardly decomposed. More preferable are hydroxyalkyl (meth)acrylates among (meth)acrylates having a hydroxyl group, (meth)acrylates having an alkoxy group in the molecule and having a structure in which the hydroxyl group of a hydroxyalkyl (meth)acrylate is replaced by an alkoxy group, and hydrophilic (meth)acrylates represented by the general formula (c) ($R^{13}$ may be hydrogen, or a group other than hydrogen). Among alkoxy groups of the (meth)acrylates having a structure in which the hydroxyl group of the hydroxyalkyl (meth)acrylate is replaced by an alkoxy group, a methoxy group and an ethoxy group are preferable, with the methoxy group being more preferable, from the viewpoint of easily obtaining a transparent silicone hydrogel.

Among the hydroxyalkyl (meth)acrylates, 2-hydroxyethyl (meth)acrylate and 2-hydroxypropyl (meth)acrylate are further preferable. Among (meth)acrylates having a structure in which the hydroxy group of the hydroxyalkyl (meth)acrylate is replaced by an alkoxy group, (meth)acrylates having a structure in which the hydroxyl group of 2-hydroxyethyl (meth)acrylate is replaced by an alkoxy group (2-alkoxyethyl (meth)acrylate), and (meth)acrylates having a structure in which the hydroxyl group of 2-hydroxypropyl (meth)acrylate is replaced by an alkoxy group (2-alkoxypropyl (meth)acrylate) are further preferable. Among hydrophilic (meth)acrylates represented by the general formula (c), polyethylene glycol mono(meth)acrylates, (meth)acrylates having a structure in which the hydroxyl group of a polyethylene glycol mono(meth)acrylate is replaced by an alkoxy group, polypropylene glycol mono(meth)acrylates, and (meth)acrylates having a structure in which the hydroxyl group of a polypropylene glycol mono(meth)acrylate is replaced by an alkoxy group are further preferable.

Among hydrophilic (meth)acrylates, hydrophilic (meth)acrylates having an alkoxy group in the molecule are preferable for adjusting the elastic modulus of the resulting silicone hydrogel to be low. More preferable are (meth)acrylates having a structure in which the hydroxyl group of a hydroxyalkyl (meth)acrylate is replaced by an alkoxy group, and hydrophilic (meth)acrylates represented by the general formula (c) and having as $R^{13}$ a group other than hydrogen. Among alkoxy groups of the (meth)acrylates having a structure in which the hydroxyl group of the hydroxyalkyl (meth)acrylate is replaced by an alkoxy group, a methoxy group and an ethoxy group are preferable, with the methoxy group being more preferable, from the viewpoint of easily obtaining a transparent silicone hydrogel.

Among (meth)acrylates having a structure in which the hydroxy group of the hydroxyalkyl (meth)acrylate is replaced by an alkoxy group, (meth)acrylates having a structure in which the hydroxyl group of 2-hydroxyethyl (meth)acrylate is replaced by an alkoxy group, and (meth)acrylates having a structure in which the hydroxyl group of 2-hydroxypropyl (meth)acrylate is replaced by an alkoxy group are further preferable. Among hydrophilic (meth)acrylates represented by the general formula (c) and having as $R^{13}$ a group other than hydrogen, (meth)acrylates having a structure in which the hydroxyl group of a polyethylene glycol mono(meth)acrylate is replaced by a methoxy group, and (meth)acrylates having a structure in which the hydroxyl group of a polypropylene glycol mono(meth)acrylate is replaced by a methoxy group are further preferable. The hydrophilic (meth)acrylate having an alkoxy group in the molecule has a structure in which the hydroxyl group is replaced by an alkoxy group such as a methoxy group, so that the number of hydrogen bonds decreases, and thus the elastic modulus of the resulting silicone hydrogel can be reduced.

Among hydrophilic (meth)acrylates, hydrophilic (meth) acrylates represented by the general formula (c) and having as $R^{13}$ a group other than hydrogen, among hydrophilic (meth)acrylates having an alkoxy group in the molecule, are preferable for adjusting the elastic modulus of the resulting silicone hydrogel to be lower. The hydrophilic (meth)acrylate represented by the general formula (c) and having as $R^{13}$ a group other than hydrogen has a structure in which the hydroxyl group is replaced by an alkoxy group such as a methoxy group, so that the number of hydrogen bonds decreases, and in addition, the hydrophilic (meth)acrylate has a side chain having a sufficient chain length and flexibility due to repetition of two or more ethylene glycol structures, and thus the elastic modulus of the resulting silicone hydrogel can be further reduced.

Among hydrophilic (meth)acrylates, hydrophilic (meth) acrylates having a hydroxyl group in the molecule are preferable for stabilizing the shape of the resulting silicone hydrogel. More preferable are hydroxyalkyl (meth)acrylates, and hydrophilic (meth)acrylates represented by the general formula (c) and having hydrogen as $R^{13}$.

Among the hydroxyalkyl (meth)acrylates, 2-hydroxyethyl (meth)acrylate and 2-hydroxypropyl (meth)acrylate are further preferable. Among hydrophilic (meth)acrylates represented by the general formula (c) and having hydrogen as $R^{13}$, polyethylene glycol mono(meth)acrylates and polypropylene glycol mono(meth)acrylates. Since these hydrophilic (meth)acrylates each have a hydroxyl group, shape stability can be improved by forming hydrogen bonds.

When the content of repeating units derived from hydrophilic (meth)acrylates, which are contained in the silicone hydrogel of the present invention, is excessively large, the oxygen permeability of the silicone hydrogel is reduced. When the content of the repeating units is excessively small, the water content is reduced, so that the silicone hydrogel is excessively hard. Therefore, the content of the repeating units is 5 to 70% by mass, more preferably 10 to 50% by mass, most preferably 20 to 40% by mass based on the mass of the silicone hydrogel. The lower limit is 5% by mass, 10% by mass or 20% by mass. The upper limit is 70% by mass, 50% by mass or 40% by mass. The lower limit and the upper limit may be combined in various ways.

When the ratio of repeating units derived from hydrophilic (meth)acrylates having a hydroxyl group in repeating units derived from hydrophilic (meth)acrylates, which are contained in the silicone hydrogel of the present invention, is excessively high, the elastic modulus of the silicone hydrogel tends to increase probably under the influence of hydrogen bonds, and therefore it is preferable that repeating units derived from hydrophilic (meth)acrylates having no hydroxyl group are included at a certain ratio in repeating units derived from hydrophilic (meth)acrylates. The content of repeating units derived from hydrophilic (meth)acrylates having no hydroxyl group is preferably 20% by mass or more, still more preferably 50% by mass or more, and most preferably 70% by mass or more based on the total number of repeating units derived from hydrophilic (meth)acrylates.

The polymerization stock solution for obtaining the silicone hydrogel of the present invention may contain reactive and non-reactive humectants.

Examples of the preferred humectant include hydrophilic polymers having a molecular weight of 1000 or more. The preferred added amount of the humectant is 1 to 30% by mass based on the mass of the silicone hydrogel.

Examples of the hydrophilic polymer that may be used in the silicone hydrogel of the present invention include poly-N-vinylpyrrolidone, poly-N-vinyl-2-piperidone, poly-N-vinyl-2-caprolactam, poly-N-vinyl-3-methyl-2-caprolactam, poly-N-vinyl-3-methyl-2-piperidone, poly-N-vinyl-4-methyl-2-piperidone, poly-N-vinyl-4-methyl-2-caprolactam, poly-N-vinyl-3-ethyl-2-pyrrolidone, poly-N-vinyl-4,5-dimethyl-2-pyrrolidone, polyvinylimidazole, poly-N-vinylformamide, poly-N-vinyl(methyl)acetamide, poly-N-methyl-N-vinyl(methyl)acetamide, poly-N-vinyl-N-(methyl)propionamide, poly-N-vinyl-N-methyl-2-(methyl) propionamide, poly-N-vinyl-2-(methyl)propionamide, poly-N-vinyl-N,N'-dimethyl urea, poly-N,N-dimethylacrylamide, poly-N,N-diethylacrylamide, poly-N-isopropylacrylamide, polyvinyl alcohol, polyacrylate, polyethylene oxide, poly-2-ethyloxazoline, heparin, polysaccharide, poly-acryloyl-morpholine, and mixtures and copolymers thereof.

A hydrophilic polymer selected from polyvinylpyrrolidone, poly-N,N-dimethylacrylamide, polyacrylic acid, polyvinyl alcohol, poly-N-methyl-N-vinyl(methyl)acetamide, and a copolymer and a mixture thereof may be effective particularly for improving the wettability of a specific silicone hydrogel. Owing to polyvinylpyrrolidone and poly-N,N-dimethylacrylamide, a balance between the wettability of the silicone hydrogel and compatibility with the polymerization stock solution is achieved at a specific proportion.

When the amount of the hydrophilic polymer to be used in the silicone hydrogel of the present invention is excessively small, it may be unable to obtain desired wettability, and when the amount of the hydrophilic polymer is excessively large, the hydrophilic polymer may be hardly dissolved in the polymerization stock solution. Therefore, the amount of the hydrophilic polymer is 1 to 30% by mass, 2 to 25% by mass in some embodiments, 3 to 20% by mass in other embodiments, and 6 to 9% by mass in other embodiments based on the mass of the silicone hydrogel. The lower limit is 1% by mass or 2% by mass, preferably 3% by mass or 6% by mass. The upper limit is 30% by mass, 25% by mass, 20% by mass or 9% by mass. The lower limit and the upper limit may be combined in various ways.

When the molecular weight of the hydrophilic polymer to be used in the silicone hydrogel of the present invention is excessively small, it may be unable to impart desired wettability, and when the molecular weight of the hydrophilic polymer is excessively large, solubility in the polymerization stock solution may be deteriorated, and the viscosity of the polymerization stock solution increases. The molecular weight is preferably 1,000 daltons to 10,000,000 daltons in one embodiment, 100,000 daltons to 1,000,000 daltons in some embodiments, and 200,000 daltons to 800,000 daltons in other embodiments. In an embodiment in which the hydrophilic polymer contains at least one reactive group which can be covalently bonded to a silicone hydrogel matrix, the molecular weight of the hydrophilic polymer may be at least 2,000 daltons or at least 5,000 daltons, and 5,000 to 180,000 daltons or 5,000 to 150,000 daltons in some embodiments. The lower limit is 1,000 daltons, 100, 000 daltons or 200,000 daltons. The upper limit is 10,000, 000 daltons, 1,000,000 daltons or 800,000 daltons. The preferred lower limit and the preferred upper limit may be combined in various ways.

The molecular weight of the hydrophilic polymer in the present invention is expressed in terms of a mass average molecular weight (Mw) measured by gel permeation chromatography (column: TSKgel GMPWXL manufactured by TOSOH CORPORATION, mobile phase/methanol=50/50 (volume ratio), 0.1 N lithium nitrate added, flow rate: 0.5 mL/minute, detector: differential refractive index detector, molecular weight standard sample: polyethylene glycol).

When the total number of repeating units derived from (meth)acrylates, which are contained in the silicone hydrogel of the present invention, is excessively small, the polymerization rates of the monomers in copolymerization are not equal, and thus the polymerization composition becomes uneven. The total amount of the repeating units should be more than 80% by mass, and is more preferably 90% by mass or more, still more preferably 95% by mass or more, and most preferably 99.5% by mass or more based on the mass of the silicone hydrogel. The total content of repeating units derived from (meth)acrylates refers to the total content of repeating units derived from monomers having (meth) acrylate groups as described above. Thus, the total content of repeating units derived from (meth)acrylates is the sum of the content of repeating units derived from monofunctional linear silicone (meth)acrylates, the content of repeating units derived from hydrophilic (meth)acrylates, and the content of all of structural units derived from other (meth)acrylates such as, for example, the above-mentioned monofunctional branched silicone (meth)acrylate if the structural units derived from the other (meth)acrylates exist. In the present invention, uniformity of the polymerization rates of the monomers in copolymerization can be confirmed by measuring a monomer consumption rate as described later.

The (meth)acrylate-based monomer is preferably a methacrylate-based monomer because a silicone hydrogel having high chemical stability is obtained. When the total number of repeating units derived from methacrylates, which are contained in the silicone hydrogel of the present invention, is excessively small, the polymerization rates of the monomers in copolymerization are not equal, and thus the polymerization composition becomes uneven. The total amount of the repeating units is preferably more than 80% by mass, more preferably 90% by mass or more, still more preferably 95% by mass or more, and most preferably 99.5% by mass or more based on the mass of the silicone hydrogel.

The (meth)acrylate-based monomer is preferably an acrylate-based monomer because a silicone hydrogel which has a low elastic modulus, is soft and has favorable comfort is obtained. When the total number of repeating units derived from acrylates, which are contained in the silicone hydrogel of the present invention, is excessively small, the polymerization rates of the monomers in copolymerization are not equal, and thus the polymerization composition becomes uneven. The total amount of the repeating units is preferably more than 80% by mass, more preferably 90% by mass or more, still more preferably 95% by mass or more, and most preferably 99.5% by mass or more based on the mass of the silicone hydrogel.

The silicone hydrogel of the present invention may also contain a repeating unit derived from a polyfunctional monomer (crosslinking monomer) having two or more polymerizable groups. In this case, the silicone hydrogel according to aspects of the present invention has solvent resistance. Preferred examples of the polyfunctional monomer having two or more polymerizable groups include difunctional or polyfunctional (meth)acrylates such as ethylene glycol di(meth)acrylate, diethylene glycol di(meth)acrylate, triethylene glycol di(meth)acrylate, tetraethylene glycol di(meth)acrylate, neopentyl glycol di(meth)acrylate, tetraethylene glycol di(meth)acrylate, 1,3-bis(3-(meth)acryloiloxypropyl)-1,1,3,3-tetramethyl-disiloxane, 1,3-bis(3-(meth)acryloiloxypropyl)-1,1,3,3-tetrakis(trimethylsiloxy)disiloxane, polydimethylsiloxanes with a (meth)acryloiloxy group at both ends, such as X-22-164A manufactured by Shin-Etsu Chemical Co., Ltd. and SILAPLANE (registered trademark) FM7711 manufactured by JNC Corporation, glyceryl tri(meth)acrylate, pentaerythritol tetra(meth)acrylate and trimethylolpropane tri(meth)acrylate; and bis-acrylamides such N,N'-methylene-bis-acrylamide, N,N'-ethylene-bis-acrylamide and N,N'-propylene-bis-acrylamide.

Among them, difunctional or polyfunctional (meth)acrylates are preferable from the viewpoint of equalizing the polymerization rate of the silicone hydrogel, difunctional (meth)acrylates are more preferable from the viewpoint of easily obtaining a silicone hydrogel having a low elastic modulus, and silicone-based di(meth)acrylates such as 1,3-bis(3-(meth)acryloiloxypropyl)-1,1,3,3-tetramethyl-disiloxane, 1,3-bis(3-(meth)acryloiloxypropyl)-1,1,3,3-tetrakis(trimethylsiloxy)disiloxane, and polydimethylsiloxanes with a (meth)acryloiloxy group at both ends, such as X-22-164A manufactured by Shin-Etsu Chemical Co., Ltd. and SILAPLANE (registered trademark) FM7711 manufactured by JNC Corporation are further preferable from the viewpoint of improving the shape recovery properties of the resulting silicone hydrogel.

When the amount of the repeating unit derived from a polyfunctional monomer having two or more polymerizable groups is excessively large, the silicone hydrogel becomes excessively hard, and when the amount of the repeating unit derived from the polyfunctional monomer is excessively small, it is difficult to maintain the shape of the silicone hydrogel. Therefore, the amount of the repeating unit derived from the polyfunctional monomer is preferably 0.1 to 25% by mass, more preferably 0.5 to 20% by mass, most preferably 0.8 to 12% based on the mass of the silicone hydrogel. The lower limit is 0.1% by mass, 0.5% by mass or 0.8% by mass. The upper limit is 25% by mass, 20% by mass or 12% by mass. The preferred lower limit and the preferred upper limit may be combined in various ways.

In preparation of the silicone hydrogel of the present invention by polymerization, a polymerization initiator may be added for accelerating polymerization. Examples of the preferred initiator include heat polymerization initiators such as peroxides and azo compounds, photopolymerization initiators (UV light photopolymerization initiators, visible light photopolymerization initiators or combinations thereof), and mixtures thereof. In the case of performing heat polymerization, an initiator having optimum decomposition characteristics at a desired reaction temperature is selected, and used. Commonly, an azo-based initiator or a peroxide-based initiator, each having a ten-hour half-life temperature of 40° C. to 120° C., is preferable. Examples of the photoinitiator include carbonyl compounds, peroxides, azo compounds, sulfur compounds, halogen compounds and metal salts.

More specific examples of the photoinitiator include aromatic α-hydroxyketone, alkoxyoxybenzoin, acetophenone, acylphosphine oxido, bisacylphosphine oxide, tertiary amine+diketone, and mixtures thereof. Further specific examples of the photoinitiator include combinations of 1-hydroxycyclohexylphenylketone, 2-hydroxy-2-methyl-1-phenyl-propane-1-one, bis(2,6-dimethoxybenzoyl)-2,4-4- trimethylpentylphosphine oxide (DMBAPO), bis(2,4,6-trimethylbenzoyl)-phenylphosphine oxide (IRGACURE (registered trademark) 819), 2,4,6-trimethylbenzyldiphenylphosphine oxide and 2,4,6-trimethylbenzoyldiphenylphosphine oxide, benzoin methyl ether and camphor quinone with ethyl 4-(N,N-dimethylamino)benzoate.

Examples of the commercially available visible light photoinitiator system include IRGACURE (registered trademark) 819, IRGACURE (registered trademark) 1700, IRGACURE (registered trademark) 1800 and IRGACURE (registered trademark) 1850 (each manufactured by BASF), and LUCIRIN TPO Initiator (manufactured by BASF). Examples of the commercially available UV light photoinitiator include DAROCUR (registered trademark) 1173 and DAROCUR (registered trademark) 2959 (manufactured by BASF). These polymerization initiators may be used alone or in combination, and the use amount thereof is about 1% by mass based on the total mass of all monomer components.

Examples of other components that may exist in a reaction mixture to be used for formation of the contact lens of the present invention include ultraviolet-absorbing compounds, pharmaceutical compounds, nutritional supplement compounds, antibacterial compounds, and copolymerizable and non-polymerizable dyes which contain dyes or compounds that are reversibly discolored or reflect light when exposed to various wavelengths of light, a releasing agent, a reactive staining agent, a pigment, a combination thereof or the like.

In preparation of the silicone hydrogel of the present invention by polymerization, a polymerization solvent may be used. The solvent may be either an organic solvent or an inorganic solvent. Examples of the solvent that can be used include water, methanol, ethanol, propanol, 2-propanol, butanol, tert-butanol, tert-amyl alcohol, and 3,7-dimethyl-3-octanol, hexanol, heptanol, octanol, nonanol, decanol, 3-methyl-3-pentanol and other alcohol-based solvents; methylene chloride and other alkyl halides; octamethyl cyclotetrasiloxane and other silanes; benzene, toluene, xylene and other types of aromatic hydrocarbon-based solvents; hexane, heptane, octane, decane, petroleum ether, kerosene, ligroin, paraffin and other types of aliphatic hydrocarbon-based solvents; acetone, methyl ethyl ketone, methyl isobutyl ketone and other ketone-based solvents; ethyl acetate, butyl acetate, methyl benzoate, dioctyl phthalate, ethylene glycol diacetate and other ester-based solvents; and diethylether, tetrahydrofuran, dioxane, ethylene glycol dialkyl ethers, diethylene glycol dialkyl ethers, triethylene glycol dialkyl ethers, tetraethylene glycol dialkyl ethers, polyethylene glycol dialkyl ethers, polyethylene glycol-polypropylene glycol block copolymers, polyethylene glycol-polypropylene glycol random copolymers and other types of glycol ether-based solvents. These solvents can be used alone or in combination.

Among these solvents, alcohol-base solvents and glycol ether-based solvents are preferable because a solvent can be easily removed from the resulting silicone hydrogel by washing with water.

The silicone hydrogel of the present invention can be molded alone in a desired shape, but can also be blended with other materials, and then molded. The surface of the molded article may be coated.

Examples of the use of the silicone hydrogel of the present invention include lenses for eye, endoscopes, catheters, infusion tubes, gas transfer tubes, stents, sheaths, cuffs, tube connectors, access ports, drainage bags, blood circuits, vulnerary covering materials and various kinds of drug carriers, and among them, contact lenses, intraocular lenses, artificial corneas, corneal inlays and corneal onlays are preferred, with contact lenses being most preferred.

When the silicone hydrogel is molded to be used as a lens for eye, the polymerization method and the molding method for the silicone hydrogel may be the following standard methods. Mention is made of, for example, a method in which a silicone hydrogel is first molded into a round-bar shape or a plate shape, and then processed into a desired shape by cutting or lathe machining; a mold polymerization method; a spin-cast method; and so on.

Preparation of a lens for eye from the silicone hydrogel of the present invention using a mold polymerization method will be described below.

A monomer composition is injected in a gap between two molds having a lens shape. Next, photopolymerization or heat polymerization is performed to form the monomer composition into a lens shape. The mold is made of resin, glass, ceramic, metal or the like, and in the case of photopolymerization, a material permeable to light having a photopolymerization wavelength, and resin or glass is usually used. In the case of producing the silicone hydrogel, a gap is formed by two facing molds, and a monomer composition is injected in the gap. The mold with the gap filled with the monomer composition is subsequently irradiated with active rays such as ultraviolet rays, visible rays or a combination thereof, or heated in an oven or a liquid bath to polymerize the monomer. A method may be used in which both photopolymerization and heating polymerization are performed in combination, for example, heating polymerization is performed after photopolymerization, or reversely, photopolymerization is performed after heating polymerization. In the case of photopolymerization, for example, the composition is generally irradiated with light including a high level of light from a light source such as a mercury lamp or a fluorescent lamp within a short time (usually 1 hour or less). In the case of performing heat polymerization, conditions of gradually raising a temperature of the composition from about room temperature and raising to a high temperature of 60° C. to 200° C. over several hours to several tens of hours are preferably used so as to maintain optical uniformity and grade of a polymer, and to enhance reproducibility.

The silicone hydrogel of the present invention can be modified by various methods. When the silicone hydrogel is to be used in a lens for eye, and does not contain a hydrophilic polymer therein, a modification treatment may be performed for improving the wettability of the lens.

Examples of the specific modification method include irradiation with electromagnetic waves (including light), plasma irradiation, vapor deposition, chemical vapor deposition treatment such as sputtering, heating, mold transfer coating, base treatment, acid treatment, and treatments with other suitable surface treatment agents, and these methods may be used in combination.

Examples of the base treatment or acid treatment include a method in which a molded article is brought into a contact with a basic or acidic solution; and a method in which a molded article is brought into a basic or acidic gas. Examples of the more specific method include a method in which a molded article is immersed in a basic or acidic solution; a method in which a basic or acidic solution or a basic or acidic gas is sprayed to a molded article; a method in which a basic or acidic solution is applied to a molded article using a spatula, a brush or the like; a method in which a molded article is spin-coated with a basic or acidic solution; and a dip coating method. The method with which the highest modification effect is obtained most conveniently is a method in which a molded article is immersed in a basic or acidic solution.

The temperature at which the silicone hydrogel is immersed in a basic or acidic solution is not particularly limited, but it is usually within the range of −50° C. to 300° C. When consideration is given to workability, the above-mentioned temperature is more preferably within the range of −10° C. to 150° C., most preferably within the range of −5° C. to 60° C.

The optimum time during which the silicone hydrogel is immersed in a basic or acidic solution varies depending on the temperature, but it is preferably within 100 hours, more preferably within 24 hours, most preferably within 12 hours. When the contact time is excessively long, not only workability and productivity are deteriorated, but also adverse influences such as reduction of oxygen permeability and deterioration of mechanical properties may be exerted.

As the base, alkali metal hydroxides, alkali earth metal hydroxides, various kinds of carbonates, various kinds of borates, various kinds of phosphates, ammonium, various kinds of ammonium salts, various kinds of amines, and high-molecular-weight bases such as polyethylene imine and polyvinyl amine can be used. Among them, alkali metal hydroxides are most preferable because they are inexpensive, and have a high treatment effect.

As the acid, various kinds of inorganic acids such as sulfuric acid, phosphoric acid, hydrochloric acid and nitric acid; various kinds of organic acids such as acetic acid, formic acid, benzoic acid and phenol; and various kinds of high-molecular-weight acids such as polyacrylic acid and polystyrenesulfonic acid. Among them, high-molecular-weight acids are most preferable because they have a high treatment effect, and minimum adverse influences on other mechanical properties.

The solvent in the basic or acidic solution may be either an inorganic solvent or an organic solvent. Examples of the solvent include water; methanol, ethanol, propanol, 2-propanol, butanol, ethylene glycol, diethylene glycol, triethylene glycol, tetraethylene glycol, polyethylene glycol, glycerin and other alcohols; benzene, toluene, xylene and other aromatic hydrocarbons; hexane, heptane, octane, decane, petroleum ether, kerosene, ligroin, paraffin and other aliphatic hydrocarbons; acetone, methyl ethyl ketone, methyl isobutyl ketone and other ketones; ethyl acetate, butyl acetate, methyl benzoate, dioctyl phthalate and other esters; and diethylether, tetrahydrofuran, dioxane, ethylene glycol dialkyl ethers, diethyl glycol dialkyl ethers, triethylene glycol dialkyl ethers, tetraethylene glycol dialkyl ethers, polyethylene glycol dialkyl ethers and other ethers; dimethylformamide, dimethylacetamide, N-methyl-2-pyrrolidone, dimethyl imidazolidinone, hexamethylphosphoric triamide, dimethylsulfoxide and other aprotic polar solvents; methylene chloride, chloroform, dichloroethane, trichloroethane, trichloroethylene and halogen-based solvents; and freon-based solvents. Among them, water is most preferable from the viewpoint of ease of economic efficiency, ease of handling, chemical stability and so on. The solvent may be a mixture of two or more solvents.

In the present invention, the basic or acidic solution to be used may contain components other than a basic or acidic substance and a solvent.

The basic or acidic substance can be removed from the silicone hydrogel by washing after the base treatment or acid treatment.

The washing solvent may be either an inorganic solvent or an organic solvent. Examples of the solvent include water; methanol, ethanol, propanol, 2-propanol, butanol, ethylene glycol, diethylene glycol, triethylene glycol, tetraethylene glycol, polyethylene glycol, glycerin and other alcohols; benzene, toluene, xylene and other aromatic hydrocarbons; hexane, heptane, octane, decane, petroleum ether, kerosene, ligroin, paraffin and other aliphatic hydrocarbons; acetone, methyl ethyl ketone, methyl isobutyl ketone and other ketones; ethyl acetate, butyl acetate, methyl benzoate, dioctyl phthalate and other esters; and diethylether, tetrahydrofuran, dioxane, ethylene glycol dialkyl ethers, diethylene glycol dialkyl ethers, triethylene glycol dialkyl ethers, tetraethylene glycol dialkyl ethers, polyethylene glycol dialkyl ethers and other ethers; dimethylformamide, dimethylacetamide, N-methyl-2-pyrrolidone, dimethyl imidazolidinone, hexamethylphosphoric triamide, dimethylsulfoxide and other aprotic polar solvents; methylene chloride, chloroform, dichloroethane, trichloroethane, trichloroethylene and halogen-based solvents; and freon-based solvents.

The washing solvent may be a mixture of two or more solvents. The washing solvent may contain components other than a solvent, for example an inorganic salt, a surfactant and a washing agent.

The above modification treatment may be applied to the whole of the silicone hydrogel, or only a part of, for example only the surface of, the silicone hydrogel. In the case of applying the modification treatment to only the surface, only the wettability of the surface can be improved without significantly changing the mechanical properties of the silicone hydrogel as a whole.

When the water content of the silicone hydrogel of the present invention is excessively low, the silicone hydrogel is becoming hard, and when the water content of the silicone hydrogel is excessively high, water is evaporated from the surface of the silicone hydrogel, so that a wearer may feel dry at the time of wearing a lens. Therefore, the water content of the silicone hydrogel is preferably 20 to 50% by mass, more preferably 25 to 45% by mass, most preferably 30 to 40% by mass. The lower limit is 20% by mass, 25% by mass or 30% by mass. The upper limit is 50% by mass, 45% by mass or 40% by mass. The preferred lower limit and the preferred upper limit may be combined in various ways.

When the silicone hydrogel according to aspects of the present invention is to be used in a lens for eye, particularly a soft contact lens, the elastic modulus of the silicone hydrogel is 200 psi or less, preferably 100 psi in some embodiments, for obtaining satisfactory comfort. The elastic modulus and elongation of the polymer in the present invention are measured by cutting out an array-type sample with a width of 5 mm at the narrowest part, and then pulling the sample at a speed of 100 mm/minute by a tension tester until the sample is broken. The initial gauge length (Lo) of the sample and the sample length (Lf) at break are measured. The tensile elastic modulus is measured at the initial linear part of a stress/strain curve. Elongation ratio=[(Lf−Lo)/Lo]×100. The elongation of the silicone hydrogel of the present invention is preferably 90% or more, 150% or more in some embodiments, and 200% or more in some embodiments. The higher the value of the elongation, the more hardly the silicone hydrogel is broken.

When the silicone hydrogel of the present invention is to be used in a lens for eye, the advance contact angle of the silicone hydrogel is preferably 70° or less, more preferably 60° or less, still more preferably 50° or less.

It is important that the silicone hydrogel of the present invention is excellent in wettability of a surface, from the viewpoint of compatibility with the living body. From such viewpoint, the liquid film retention time of a surface of the silicone hydrogel is preferably long. As used herein, the liquid film retention time is the time during which a liquid film on a surface of the silicone hydrogel (a diameter direction in the case of a lens for eye) is held without being broken, when the silicone hydrogel immersed in a borate buffer is pulled up from the borate buffer and then held in air so that a diameter direction becomes vertical. The liquid film retention time is preferably 5 seconds or more, more preferably 10 seconds or more, and most preferably 20 seconds or more. As used herein, the diameter is the diameter of a circle composed of an edge portion of a lens. The liquid film retention time is measured using a sample in a state of being wetted with a borate buffer.

Since the silicone hydrogel of the present invention is suitable for use in a lens for eye, the diameter of the silicone hydrogel of the present invention is preferably 6 mm or more and 25 mm or less, and particularly when the silicone hydrogel is to be used as a soft contact lens, it is more preferably in the form of a spherical crown having a diameter of 10 mm or more and 17 mm or less, and most preferably in the form of a spherical crown having a diameter of 13 mm or more and 15 mm or less. The lower limit is preferably 6 mm, more preferably 10 mm, and most preferably 13 mm. The upper limit is preferably 25 mm, more preferably 17 mm, and most preferably 15 mm. The preferred lower limit and the preferred upper limit may be combined in various ways.

For the oxygen permeability of the silicone hydrogel of the present invention, the oxygen permeability coefficient is preferably $40 \times 10^{-11}$ (cm$^2$/second) mLO$_2$/(mL·hPa) or more, and $50 \times 10^{-11}$ (cm$^2$/second) mLO$_2$/(mL·hPa) or more. The oxygen permeability coefficient of the polymer of the present invention is a value measured by polarography.

For the transparency of the silicone hydrogel of the present invention, the total light transmittance in a visible range is preferably 85% or more, more preferably 90% or more, and most preferably 95% or more, when the silicone hydrogel is to be used in a lens for eye.

In the case of visual observation, the score of the transparency of the silicone hydrogel of the present invention is preferably 5 or 4, more preferably 5. The evaluation method is described in examples.

The silicone hydrogel of the present invention is suitable for use in medical devices such as lenses for eye, endoscopes, catheters, infusion tubes, gas transfer tubes, stents, sheaths, cuffs, tube connectors, access ports, drainage bags, blood circuits, vulnerary covering materials and various kinds of drug carriers, particularly contact lenses, lenses for eye and artificial corneas.

EXAMPLES

The present invention will be described further in detail below by way of Examples, but the present invention is not limited to these examples.

(Measurement Method)

(1) Total Light Transmittance

The total light transmittance was measured using a SM color computer (Model: SM-7-CH, manufactured by Suga Test Instruments Co., Ltd.). A contact lens sample in a wet state was set in an optical path to make a measurement. The thickness was measured using ABC Digimatic Indicator (ID-C112, manufactured by Mitutoyo Corporation), and samples having a thickness of 0.14 to 0.15 mm were measured.

(2) Transparency

The transparency of a sample in a state of being wetted with a borate buffer was visually observed, and evaluated based on five grades in accordance with the following criteria.
5: Transparent and not turbid.
4: Faintly white-turbid.
3: Slightly white-turbid and semi-transparent.
2: White-turbid and not transparent at all.
1: Fully white.

(3) Elastic Modulus/Elongation

Array-type samples with a width of 5 mm at the narrowest part were cut out from a contact lens sample in a wet state, the thickness was measured using ABC Digimatic Indicator (ID-C112, manufactured by Mitutoyo Corporation), and the elastic modulus and the elongation were then measured by Tensilon (RTM-100 manufactured by Toyo Baldwin Co., Ltd, cross-head speed: 100 mm/minute).

(4) Zero-Stress Time

Strip-shaped samples of 5 mm in width and 1.5 cm in length were cut out from near the center of a contact lens sample in a wet state, and then measurement was performed using a rheometer CR-500DX manufactured by Sun Scientific Co., Ltd. Each sample was mounted with a chuck width set at 5 mm, and then the cycle of pulling the sample at a speed of 100 mm/minute by 5 mm and returning the sample to an initial length (5 mm) at the same speed was repeated three times. Length of time from a point of time at which stress during the second returning of the sample to the initial length becomes zero to a point of time at which stress begins to be applied (stress increases from zero) after initiation of the third pulling cycle was determined, and the obtained length of time was regarded as a zero-stress time. The shorter the zero-stress time, the better the shape recovery properties of the silicone hydrogel, and the value of the zero-stress time is preferably 2.0 seconds or less, more preferably 1.8 seconds or less, and most preferably 1.5 seconds or less.

(5) Water Content

The mass (W1) of the silicone hydrogel in a wet state and the mass (W2) in a dry state were measured, and the water content was calculated from the following equation.

$$\text{Water content (\%)} = (W1 - W2)/W1 \times 100$$

(6) Wet State

In the present invention, the wet state means a state where a sample is immersed in a borate buffer at room temperature (25° C.) for 24 hours or more. The measurement of mechanical properties in a wet state is performed as soon as possible after the borate buffer on the surface is wiped off with a clean cloth as soon as possible after the sample is taken out from the borate buffer.

(7) Dry State

In the present invention, the dry state means a state where a sample in a wet state is dried at 40° C. for 16 hours or more by a vacuum dryer. The measurement of mechanical properties in a dry state is performed as soon as possible after the sample is taken out from the dryer as soon as possible.

(8) Dynamic Contact Angle

Strip-shaped samples with a width of 5 mm were cut out from a contact lens sample in a wet state, and the dynamic contact angle with respect to a borate buffer (immersion speed: 7 mm/minute) using a dynamic contact angle meter WET-6000 manufactured by RHESCA CO., LTD.

(9) Wettability

A contact lens sample was immersed in a borate buffer in a beaker at room temperature (25° C.) for 24 hours or more. The beaker containing the specimen and the borate buffer was exposed to ultrasonic using an ultrasonic cleaner (for 1 minute). The specimen was pulled up from the borate buffer and the specimen was held in air so that a surface becomes vertical. A state of the surface of the specimen was visually observed, and the retention time of a liquid film on the surface was measured. The liquid film retention time is preferably 5 seconds or more, more preferably 10 seconds or more, and most preferably 20 seconds or more. The diameter is a diameter of a circle formed by an edge portion of a contact lens.

(10) Borate Buffer

In the present invention, a borate buffer is a "salt solution" disclosed in Example 1 of Kohyo (National Publication of Translated Version) No. 2004-517163. Specifically, it is an aqueous solution in which 8.48 g of sodium chloride, 9.26 g of boric acid, 1.0 g of sodium borate (sodium tetraborate decahydrate), and 0.10 g of ethylenediaminetetraacetic acid are dissolved in pure water to make 1,000 mL.

(11) Diameter

The diameter of an enlarged image (magnification: 10) of a contact lens sample projected using a universal projector V-10A (manufactured by Nikon Corporation) with the contact lens sample immersed in a fixed amount of a borate buffer in a Petri dish was measured by a ruler, and divided by 10, and the value thus obtained was recorded as a lens diameter.

Example 1

A silicone monomer (SILAPLANE (registered trademark) FM0711, average molecular weight: 1000, manufactured by JNC Corporation, 1.3202 g, 33 parts by mass) represented by the following formula (s1):

[Chemical Formula 8]

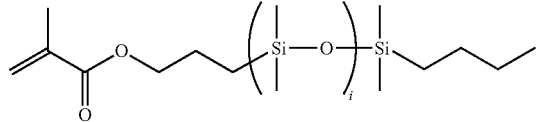

(s1)

a silicone monomer (0.8801 g, 22 parts by mass) represented by the following formula (s2):

[Chemical Formula 9]

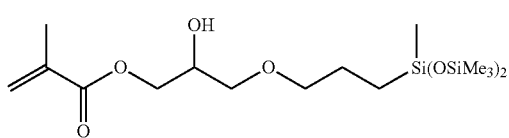

(s2)

polyethylene glycol monomethyl ether methacrylate (BLEMMER (registered trademark) PME200, q≈4, manufactured by NOF CORPORATION, 1.2614 g, 31.53 parts by mass) represented by the following formula (h1):

[Chemical Formula 10]

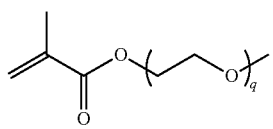

(h1)

2-hydroxyethyl methacrylate (0.3200 g, 8 parts by mass), a siloxane (manufactured by Shin-Etsu Chemical Co., Ltd., 0.3200 g, 8 parts by mass) having a methacryloyloxy group on both ends, the siloxane being represented by the following formula (c1):

[Chemical Formula 11]

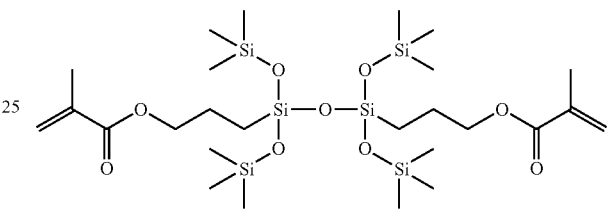

(c1)

2-(2'-hydroxy-5'-methacryloyloxyethylphenyl)-2H-benzo triazole (0.0880 g, 2.2 parts by mass) as an ultraviolet absorbing agent, t-amyl alcohol (TAA, 1.8002 g, 45 parts by mass) and IRGACURE (registered trademark) 819 (0.0100 g, 0.25 parts by mass) as a photoinitiator were blended, and mixed. The obtained monomer blend was degassed under an argon environment. In a glove boxy under a nitrogen environment, the monomer blend was injected in a gap in a mold made of lens-shaped transparent resin (front curve side: ZEONOR (registered trademark), base curve side: polypropylene), and irradiated with light (PHILIPS TL03, 1.6 mW/cm², 15 minutes) to cure the monomer blend, thereby obtaining a lens. The obtained lens was separated from the mold, and immersed a 70% (volume ratio) 2-propanol (IPA) aqueous solution at room temperature for 70 minutes to extract impurities such as residual monomers. The sample was immersed in water for 10 minutes, and then immersed in 1.2% by mass of polyacrylic acid (PAA, molecular weight: 250,000) for 30 minutes. Surplus PAA was rinsed off with pure water, the sample was then sunk in a borate buffer in a 5 mL vial, and the vial was placed in an autoclave to boil the sample at 120° C. for 30 minutes.

The diameter, transparency, wettability, water content, elongation, elastic modulus and zero-stress time of the obtained lens sample are as shown in Table 2. A lens which was transparent and had a favorable mechanical property balance was obtained.

TABLE 1

| | Composition | | | | | | | | |
|---|---|---|---|---|---|---|---|---|---|
| | Silicone monomer 1 | | Silicone monomer 2 | | Hydrophilic monomer 1 | | Hydrophilic monomer 2 | | Crosslinking monomer |
| | Formula | Parts by mass | Formula | Parts by mass | Formula | Parts by mass | Formula | Parts by mass | Formula | Parts by mass |
| Example 1 | Formula (s1) | 33 | Formula (s2) | 22 | Formula (h1) q ≈ 4 | 31.53 | HEMA | 8 | Formula (c1) | 8 |
| Example 2 | Formula (s1) | 33 | Formula (s2) | 22 | Formula (h1) q ≈ 4 | 31.53 | HEMA | 8 | Formula (c1) | 10 |

TABLE 1-continued

| | Composition | | | | | | | | |
|---|---|---|---|---|---|---|---|---|---|
| | Silicone monomer 1 | | Silicone monomer 2 | | Hydrophilic monomer 1 | | Hydrophilic monomer 2 | | Crosslinking monomer | |
| | Formula | Parts by mass | Formula | Parts by mass | Formula | Parts by mass | Formula | Parts by mass | Formula | Parts by mass |
| Example 3 | Formula (s1) | 33 | Formula (s3) | 22 | Formula (h1) q ≈ 4 | 31.53 | HEMA | 8 | Formula (c1) | 8 |
| Example 4 | Formula (s1) | 33 | Formula (s3) | 22 | Formula (h1) q ≈ 4 | 31.53 | HEMA | 8 | Formula (c1) | 10 |
| Example 5 | Formula (s1) | 33 | Formula (s3) | 22 | Formula (h1) q ≈ 4 | 31.53 | HEMA | 8 | Formula (c2) | 6 |
| Example 6 | Formula (s1) | 33 | Formula (s3) | 22 | Formula (h1) q ≈ 4 | 31.53 | HEMA | 8 | Formula (c2) | 7 |
| Example 7 | Formula (s1) | 33 | Formula (s2) | 22 | Formula (h1) q ≈ 4 | 31.53 | HEMA | 8 | Formula (c2) | 5 |
| Example 8 | Formula (s1) | 33 | Formula (s2) | 22 | Formula (h1) q ≈ 4 | 31.53 | HEMA | 8 | Formula (c2) | 6 |
| Example 9 | Formula (s1) | 33 | Formula (s2) | 22 | Formula (h1) q ≈ 4 | 31.53 | HEMA | 8 | X-22-164A | 8 |
| Example 10 | Formula (s1) | 33 | Formula (s3) | 22 | Formula (h1) q ≈ 4 | 31.53 | HEMA | 8 | X-22-164A | 10 |
| Example 11 | Formula (s1) | 33 | Formula (s3) | 22 | Formula (h1) q ≈ 4 | 31.53 | HEMA | 8 | 4G | 6 |
| Example 12 | Formula (s1) | 33 | Formula (s2) | 22 | Formula (h1) q ≈ 4 | 31.53 | HEMA | 8 | Formula (c2) | 4 |
| Example 13 | Formula (s1) | 33 | Formula (s2) | 22 | Formula (h1) q ≈ 2 | 31.53 | HEMA | 8 | Formula (c2) | 4 |
| Example 14 | Formula (s1) | 33 | Formula (s2) | 22 | Formula (h1) q ≈ 9 | 31.53 | HEMA | 8 | Formula (c2) | 4 |
| Example 15 | Formula (s1) | 33 | Formula (s2) | 22 | Formula (h1) q ≈ 1 | 31.53 | HEMA | 8 | Formula (c2) | 4 |
| Example 16 | Formula (s1) | 33 | Formula (s2) | 22 | Formula (h2) | | 31.53 | HEMA | 8 | Formula (c2) | 4 |
| Example 17 | Formula (s1) | 33 | Formula (s2) | 22 | Formula (h3) | | 31.53 | HEMA | 8 | Formula (c2) | 4 |
| Comparative Example 1 | Formula (s1) | 0 | Formula (s3) | 55 | Formula (h1) q ≈ 4 | 31.53 | HEMA | 8 | 4G | 6 |

TABLE 2

| | Measured value | | | | | | |
|---|---|---|---|---|---|---|---|
| | Diameter (mm) | Transparency | Wettability (seconds) | Water Content (%) | Elongation (%) | Elastic modulus (psi) | Zero-Stress Time (sec) |
| Example 1 | 13.5 | 5 | 53 | 19.7 | 174 | 115 | 1.75 |
| Example 2 | 13.4 | 5 | 60 | 17.3 | 153 | 156 | 1.89 |
| Example 3 | 13.8 | 4 | 36 | 24.0 | 203 | 57 | 1.61 |
| Example 4 | 13.5 | 5 | 52 | 18.1 | 98 | 106 | 1.70 |
| Example 5 | 13.6 | 5 | 60 | 23.7 | 207 | 90 | 1.60 |
| Example 6 | 13.5 | 5 | 60 | 19.5 | 134 | 135 | 1.38 |
| Example 7 | 13.7 | 5 | 60 | 26.7 | 175 | 79 | 1.92 |
| Example 8 | 13.5 | 5 | 60 | 22.8 | 165 | 120 | 1.81 |
| Example 9 | 13.6 | 5 | 10.2 | 22.8 | 265 | 71 | 1.53 |
| Example 10 | 13.4 | 5 | NA | 23.5 | 294 | 47 | 1.56 |
| Example 11 | 13.5 | 5 | 60 | 22.6 | 166 | 92 | 1.29 |
| Example 12 | 13.7 | 4 | 60 | 22.6 | 215 | 77 | 1.66 |
| Example 13 | 14.9 | 5 | 4.4 | 3.7 | 247 | 218 | 2.11 |
| Example 14 | 15.5 | 3 | 60 | 51.6 | 140 | 52 | 1.81 |
| Example 15 | 12.5 | 5 | 1.7 | 1.5 | 219 | 721 | 3.39 |
| Example 16 | 12.4 | 4 | 1.0 | 1.0 | 303 | 458 | 2.90 |
| Example 17 | 12.8 | 5 | 2.8 | 5.1 | 53 | 775 | 3.49 |
| Comparative Example 1 | 13.2 | 4 | 56 | 19.5 | 294 | 233 | 2.72 |

Example 2

In the same manner as in Example 1, except that the composition was changed as shown in Table 1, polymerization was performed to obtain a lens sample. The diameter, transparency, wettability, water content, elongation, elastic modulus and zero-stress time of the obtained sample were as shown in Table 2.

Examples 3 and 4

In the same manner as in Example 1, except that the silicone monomer in Example 1 was changed to one represented by the formula (s3), and the composition was changed as shown in Table 1, polymerization was performed to obtain a lens sample. The diameter, transparency, wettability, water content, elongation, elastic modulus and zero-stress time of the obtained sample are as shown in Table 2.

[Chemical Formula 12]

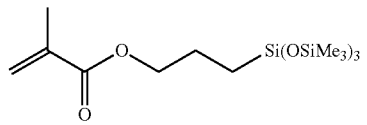

(s3)

Examples 5 to 8

In the same manner as in Example 1, except that the silicone monomer in Example 1 was changed as shown in Table 1, and the crosslinking monomer was changed to a crosslinking monomer represented by the following formula (c2):

[Chemical Formula 13]

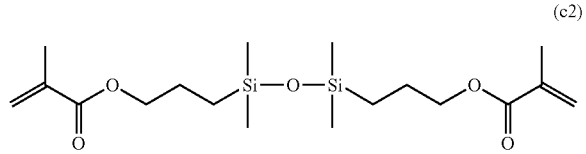

(c2)

polymerization was performed to obtain a lens sample. The diameter, transparency, wettability, water content, elongation, elastic modulus and zero-stress time of the obtained sample are as shown in Table 2.

Examples 9 and 10

In the same manner as in Example 1, except that the silicone monomer in Example 1 was changed as shown in Table 1, the crosslinking monomer was changed to X-22-164A manufactured by Shin-Etsu Chemical Co., Ltd., and the composition was changed as shown in Table 1, polymerization was performed to obtain a lens sample. The diameter, transparency, wettability, water content, elongation, elastic modulus and zero-stress time of the obtained sample are as shown in Table 2.

Example 11

In the same manner as in Example 1, except that the silicone monomer in Example 1 was changed as shown in Table 1, the crosslinking monomer was changed to tetraethylene glycol dimethacrylate (4G), and the composition was changed as shown in Table 1, polymerization was performed to obtain a lens sample. The diameter, transparency, wettability, water content, elongation, elastic modulus and zero-stress time of the obtained sample are as shown in Table 2.

Example 12

In the same manner as in Example 1, except that the crosslinking monomer was changed to a crosslinking monomer represented by the formula (c2), and the composition was changed as shown in Table 1, polymerization was performed to obtain a lens sample. The diameter, transparency, wettability, water content, elongation, elastic modulus and zero-stress time of the obtained sample are as shown in Table 2.

Example 13

In the same manner as in Example 12, except that the hydrophilic monomer was changed to polyethylene glycol monomethyl ether methacrylate (BLEMMER PME100, q≈2, manufactured by NOF CORPORATION, 1.2614 g, 31.53 parts by mass) represented by the formula (h1), polymerization was performed to obtain a lens sample. The diameter, transparency, wettability, water content, elongation, elastic modulus and zero-stress time of the obtained sample are as shown in Table 2.

Example 14

In the same manner as in Example 12, except that the hydrophilic monomer was changed to polyethylene glycol monomethyl ether methacrylate (BLEMMER PME400, q≈9, manufactured by NOF CORPORATION, 1.2614 g, 31.53 parts by mass) represented by the formula (h1), polymerization was performed to obtain a lens sample. The diameter, transparency, wettability, water content, elongation, elastic modulus and zero-stress time of the obtained sample are as shown in Table 2.

Example 15

In the same manner as in Example 12, except that the hydrophilic monomer was changed to 2-methoxyethylmethacrylate (q=1, manufactured by Tokyo Chemical Industry Co., Ltd., 1.2614 g, 31.53 parts by mass) represented by the formula (h1), polymerization was performed to obtain a lens sample. The diameter, transparency, wettability, water content, elongation, elastic modulus and zero-stress time of the obtained sample are as shown in Table 2.

Example 16

In the same manner as in Example 12, except that the hydrophilic monomer was changed to 2-ethoxyethyl methacrylate (manufactured by Tokyo Chemical Industry Co., Ltd., 1.2614 g, 31.53 parts by mass) represented by the following formula (h2), polymerization was performed to obtain a lens sample. The diameter, transparency, wettability, water content, elongation, elastic modulus and zero-stress time of the obtained sample are as shown in Table 2.

[Chemical Formula 14]

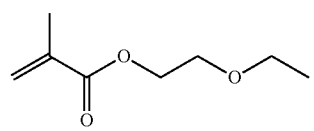

(h2)

Example 17

In the same manner as in Example 12, except that the hydrophilic monomer was changed to 2-hydroxypropyl methacrylate (manufactured by Wako Pure Chemical Industries, Ltd., 1.2614 g, 31.53 parts by mass) represented by the following formula (h3), polymerization was performed to obtain a lens sample. The diameter, transparency, wettability, water content, elongation, elastic modulus and zero-stress time of the obtained sample are as shown in Table 2.

[Chemical Formula 15]

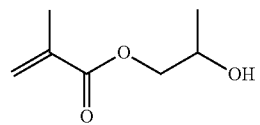

(h3)

Comparative Example 1

In the same manner as in Example 11, except that the composition in Example 11 was changed to a composition that does not include a monofunctional linear silicone methacrylate of the formula (s1), as shown in Table 1, polymerization was performed to obtain a lens sample. The diameter, transparency, wettability, water content, elongation, elastic modulus and zero-stress time of the obtained sample are as shown in Table 2.

Example 18

(1) GPC Measurement

GPC measurement was performed under the following conditions.

Apparatus: Prominence GPC system, manufactured by Shimadzu Corporation
Pump: LC-20AD
Auto-sampler: SIL-20AHT
Column oven: CTO-20A
Detector: RID-10A
Column: GMPWXL manufactured by TOSOH CORPORATION (7.8 mm in inner diameter×30 cm, 13 µm in particle diameter)
Solvent: Water/methanol=50/50 (volume ratio, addition of 0.1N lithium nitrate)
Flow rate: 0.5 mL/minute
Measurement time: 30 minutes
Sample concentration: 0.1% by mass
Injection amount: 100 µL
Standard sample: Polyethylene oxide standard sample, manufactured by Agilent (0.1 kD to 1,258 kD)

(2) Calculation of Monomer Consumption Rate

A silicone monomer (27.50 g, 26.03%) represented by the formula (s2), BLEMMER PME200 (18.74 g, 17.74% by mass), HEMA (3.99 g, 3.78% by mass), 2,2'-azobis(2,4-dimethylvaleronitrile) (polymerization initiator, 0.2552 g, 0.24% by mass), t-amyl alcohol (54.96 g, 52.03% by mass) and dodecyl mercaptan (0.19 g, 0.18% by mass) were mixed in a four-neck flask to prepare a polymerization solution. The four-neck flask was immersed in a water bath heated to 60° C., and the time point at which the flask was immersed was defined as 0 minute. 100 µL of a sample was extracted from the reaction solution at each of time points: 0 minute, 20 minutes, 40 minutes, 60 minutes, 80 minutes, 100 minutes, 120 minutes, 150 minutes, 180 minutes, 240 minutes, 300 minutes, 360 minutes and 720 minutes, and a solution having the same composition as that of the mobile phase in the GPC measurement in 1) was added to obtain a GPC sample. For each sample of the reaction solution, GPC measurement was performed in the same manner as in (1).

On the basis of the peak areas for the silicone monomer of the formula (s2), BLEMMER PME200 (PME200) and HEMA, the weight of the extracted sample and the weight of the HPLC sample, the consumption rates of both the monomers were calculated. A graph is plotted between the polymerization time (T) and the monomer consumption rate (M) (FIG. 1) to prepare a consumption rate curve for both the monomers. The result showed that the polymerization rates of the methacrylates used for polymerization were equal.

In the case where measurement by GPC is difficult, HPLC measurement may be performed, for example, under the following conditions, followed by calculating the monomer consumption rate.

Apparatus: Prominence HPLC system manufactured by Shimadzu Corporation
Pump: LC-20AD
Auto-sampler: SIL-20AHT
Detector: SPD-20A (detection wavelength: 254 nm)
Column: Agilent Zorbax Eclipse XDB C18 (4.6 mm×75 mm, 3.5 µm)
Solvent A: Acetonitrile
Solvent B: Water
Solvent gradient: solvent A/solvent B=50/50 (0 minute)→50/50 (3 minutes)→100/0 (5 minutes)→100/0 (12 minutes)→50/50 (15 minutes)→50/50 (20 minutes)
Flow rate: 1.3 mL/minute
Injection amount: 5 µL
Column temperature: 35° C.
Analysis time: 20 minutes When in the case of calculating the monomer consumption rate in other monomer compositions, the monomer consumption rate cannot be calculated under the above-mentioned HPLC measurement conditions because the peaks of monomers overlap each other, the detection wavelength is not appropriate, or the like, the conditions may be appropriately changed to conditions under which measurement can be performed, followed by calculating the monomer consumption rate.

Comparative Example 2

In the same manner as in Example 18, except that BLEMMER PME200 in Example 18 was replaced by N,N-dimethylacrylamide (DMA) as a hydrophilic acrylamide, experiments were conducted to prepare a monomer consumption rate curve (FIG. 2). The results suggested that there was a difference in polymerization rate between DMA and other monomers, and thus the resulting copolymer had different compositions in the initial stage of polymerization and in the end stage of polymerization.

Accordingly, the silicone hydrogel of the present invention is suitable for use in medical devices, and particularly suitable for use in contact lenses, intraocular lenses, artificial corneas and so on.

The invention claimed is:

1. A silicone hydrogel comprising a repeating unit derived from a monofunctional linear silicone (meth)acrylate and a repeating unit derived from a hydrophilic (meth)acrylate wherein
   the content of the repeating units derived from the (meth)acrylates is more than 80% by mass; and
   the ratio of a repeating unit derived from a hydrophilic (meth)acrylate having no hydroxyl group in the repeating units as a fraction of the total amount of hydrophilic (meth)acrylates is 20% by mass or more.

2. The silicone hydrogel according to claim 1, wherein the monofunctional linear silicone (meth)acrylate is represented by the following general formula (a):

[Chemical Formula 1]

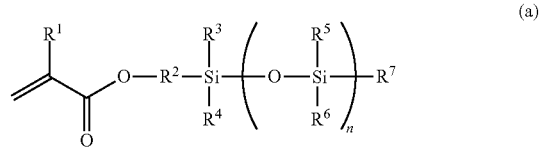

(a)

wherein $R^1$ represents hydrogen or a methyl group; $R^2$ represents an optionally substituted divalent organic group having 1 to 20 carbon atoms; $R^3$ to $R^6$ each independently represent an optionally substituted alkyl group having 1 to 20 carbon atoms or an optionally substituted aryl group having 6 to 20 carbon atoms; $R^7$ represents an optionally substituted alkyl group having 1 to 20 carbon atoms or an optionally substituted aryl group having 6 to 20 carbon atoms; and n represents an integer of 1 to 200 which optionally has distribution.

3. The silicone hydrogel according to claim 1, further comprising a repeating unit derived from a monofunctional silicone (meth) acrylate different from the monofunctional linear silicone (meth)acrylate.

4. The silicone hydrogel according to claim 1, wherein the content of the repeating unit derived from the silicone (meth)acrylate is 30 to 95% by mass.

5. A silicone hydrogel comprising a repeating unit derived from a monofunctional linear silicone (meth)acrylate and a repeating unit derived from a hydrophilic (meth)acrylate, wherein the content of the repeating units derived from the (meth) acrylates is more than 80% by mass; the hydrophilic (meth)acrylate has a group selected from the group consisting of a hydroxyl group, an alkoxy group, a carboxy group and a sulfonic acid group in the molecule; and the hydrophilic (meth)acrylate is represented by the following general formula (c): [Chemical Formula 2]

wherein $R^8$ represents hydrogen or a methyl group; $R^9$ to $R^{12}$ each independently represent hydrogen, an optionally substituted alkyl group having 1 to 20 carbon atoms, or an optionally substituted aryl group having 6 to 20 carbon atoms; $R^{13}$ represents hydrogen, an optionally substituted alkyl group having 1 to 20 carbon atoms, or an optionally substituted aryl group having 6 to 20 carbon atoms; and m represents an integer of 2 to 100 which optionally has distribution.

6. The silicone hydrogel according to claim 1, wherein the content of the repeating unit derived from the hydrophilic (meth)acrylate is 5 to 70% by mass.

7. The silicone hydrogel according to claim 1, comprising a repeating unit derived from a polyfunctional (meth)acrylate.

8. The silicone hydrogel according to claim 7, wherein the content of the repeating unit derived from the polyfunctional (meth)acrylate is 0.05 to 10% by mass.

9. A medical device which is produced using the silicone hydrogel according to claim 1.

10. The medical device according to claim 9, wherein the medical device is a lens for eye.

11. The medical device according to claim 10, wherein the lens for eye is a contact lens.

* * * * *